US008828002B2

(12) United States Patent
Lesinski et al.

(10) Patent No.: US 8,828,002 B2
(45) Date of Patent: Sep. 9, 2014

(54) FENESTRATION BURR

(75) Inventors: S. George Lesinski, Cincinnati, OH (US); Gregory N. Koskowich, Pleasanton, CA (US)

(73) Assignee: OtoKinetics Inc., Salt Lake City, UT (US)

( * ) Notice: Subject to any disclaimer, the term of this patent is extended or adjusted under 35 U.S.C. 154(b) by 174 days.

(21) Appl. No.: 13/355,460

(22) Filed: Jan. 20, 2012

(65) Prior Publication Data
US 2013/0190764 A1 Jul. 25, 2013

(51) Int. Cl.
*A61B 17/00* (2006.01)
(52) U.S. Cl.
USPC .............................. 606/80; 606/172; 606/180
(58) Field of Classification Search
USPC .............. 606/79, 80, 172, 180; 623/10; 60/58
See application file for complete search history.

(56) References Cited

U.S. PATENT DOCUMENTS

| 3,688,386 A | 9/1972 | Pereira |
| 4,498,461 A | 2/1985 | Hakansson |
| 4,606,329 A | 8/1986 | Hough |
| 5,772,575 A | 6/1998 | Lesinski et al. |
| 5,951,601 A | 9/1999 | Lesinski et al. |
| 6,068,589 A | 5/2000 | Neukermans |
| 8,147,544 B2 | 4/2012 | Lesinski et al. |
| 2005/0149085 A1 | 7/2005 | Robison et al. |
| 2007/0260254 A1 | 11/2007 | Lesinski |
| 2008/0215148 A1 | 9/2008 | Lesinski et al. |
| 2010/0042184 A1 | 2/2010 | Daglow |
| 2012/0245585 A1* | 9/2012 | Kaiser et al. .................... 606/80 |

OTHER PUBLICATIONS

International Search Report and Written Opinion for International Application No. PCT/US2013/022000, mailed Mar. 22, 2013.

* cited by examiner

*Primary Examiner* — Andrew Yang
(74) *Attorney, Agent, or Firm* — Nixon Peabody LLP

(57) ABSTRACT

A cochlear fenestration burr includes a shaft oriented along a longitudinal axis of rotation of the burr, a cylindrical depth stop member oriented along the axis, the depth stop member having a thickness dimension, a diameter dimension and a contact surface, an extension member extended outward from the contact surface and coaxial with the axis, a cutting member having a cutting surface supported by the extension member, and a cutting tip at the end of the cutting member in the center of the cutting surface and coaxial with the axis. A maximum cutting depth is defined by a distance along the axis between an end of the cutting tip and the contact surface. A cutting grit is disposed on the cutting tip and cutting surface.

8 Claims, 1 Drawing Sheet

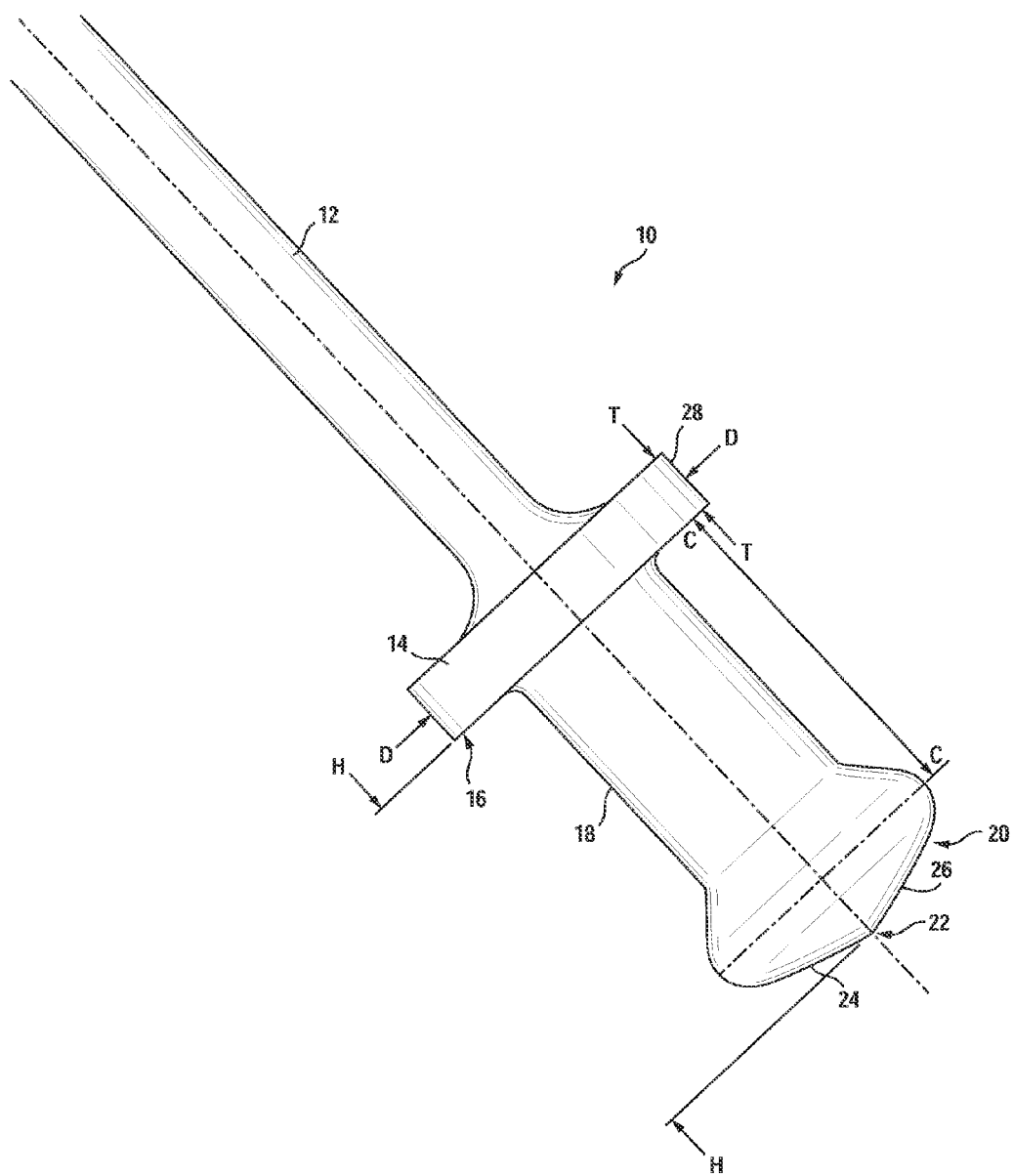

FENESTRATION BURR

TECHNICAL FIELD

The present disclosure relates generally to a cochlear fenestration burr.

BACKGROUND

A cochlear fenestration burr is a specialized surgical drill for use in drilling a hole or fenestration in the otic capsule bone adjacent to the scala tympani of the cochlea. Existing surgical drills are used by otologists to fenestrate the cochlea for the purpose of inserting an electrode that is part of a cochlear implant. In the case of such a cochlear implant there is little concern about damaging the internal structures of the cochlea while drilling because inserting the electrode will cause damage in any event. Accordingly the existing fenestration burrs have no guard or drill stop of any sort.

For fully implantable hearing aids, it is important when fenestrating the cochlea not to damage the basilar membrane or organ of corti. Accordingly, a different approach to fenestration burrs will be required.

Overview

A cochlear fenestration burr includes a shaft oriented along a longitudinal axis of rotation of the burr, a cylindrical depth stop member oriented along the axis, the depth stop member having a thickness dimension, a diameter dimension and a contact surface, an extension member extended outward from the contact surface and coaxial with the axis, a cutting member having a cutting surface supported by the extension member, and a cutting tip at the end of the cutting member in the center of the cutting surface and coaxial with the axis. A maximum cutting depth is defined by a distance along the axis between an end of the cutting tip and the contact surface. A cutting grit is disposed on the cutting tip and cutting surface.

BRIEF DESCRIPTION OF THE DRAWINGS

The accompanying drawings, which are incorporated into and constitute a part of this specification, illustrate one or more examples of embodiments and, together with the description of example embodiments, serve to explain the principles and implementations of the embodiments.

In the drawings:

FIG. 1 is a front perspective drawing showing a cochlear fenestration burr in accordance with an embodiment.

DESCRIPTION OF EXAMPLE EMBODIMENTS

Example embodiments are described herein in the context of a fenestration burr for use in creating a fenestration of the cochlea of a patient for use, for example, with a fully implantable hearing aid. Those of ordinary skill in the art will realize that the following description is illustrative only and is not intended to be in any way limiting. Other embodiments will readily suggest themselves to such skilled persons having the benefit of this disclosure. Reference will now be made in detail to implementations of the example embodiments as illustrated in the accompanying drawings. The same reference indicators will be used to the extent possible throughout the drawings and the following description to refer to the same or like items.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

In accordance with an embodiment of the invention a specialized cochlear fenestration burr 10 for use in preparing the cochlea of a patient to receive a fully implantable hearing aid is illustrated (not to scale) in FIG. 1. The body of burr 10 may be fabricated, for example, out of a suitable material such as titanium or steel. The burr 10 includes a shaft 12 oriented about a longitudinal axis 13, a depth stop member 14 having a contact surface 16 an extension 18 supporting a cutting member 20 having a pointed tip 22 at the end thereof. Shaft 12 is configured for attachment to a powered drill device. The depth stop member 14 has a diameter dimension D-D and a thickness dimension T-T and defines a height dimension H-H with the pointed tip 22 defining a cutting depth and sized so as to limit penetration of the burr 10 into the patient. Pointed tip 22 allows the burr to avoid slippage during cutting and allows precise placement of the burr prior to cutting. Tip 22 and at least the surrounding surface 24 of cutting member 20 are coated with a cutting grit 26, such as diamond grit or another suitable cutting agent to provide cutting action. Cutting member 20 has a maximum diameter dimension of 1.50 mm in one embodiment which yields a fenestration of about 1.54-1.56 mm in practice. Cutting member 20 is preferably not cylindrical in shape in part so as to limit unnecessary widening of the fenestration during cutting. The maximum diameter of extension 18 is not critical except that it should be less than the maximum diameter of cutting member 20. This facilitates flushing the area being drilled with saline solution which is then removed with a suction device to remove bone dust and cool the bone during the drilling operation. The dimension C-C is defined as the distance parallel to the longitudinal axis 13 between the circle of maximum diameter 15 of cutting member 20 and contact surface 16. In one embodiment CC is 2.00 mm.

Using a depth stop limits damage to the internal structure of the cochlea. The distance H-H from the pointed tip 22 of the burr 10 to the contact surface 16 of the depth stop member 14 should be less than about 2.5 mm.

Using edge 28 of the depth stop member 14 as a guide helps to ensure that the fenestration is located in the desired position in the scala tympani. The diameter D-D of the depth stop member 14 should be less than about 4.0 mm.

The thickness T-T of the depth stop member 14 is selected so that the burr 10 can make the fenestration slightly "behind" the external canal wall. Thus the cylindrical depth stop member 14 should have a maximum diameter D-D of about 4.0 mm and a thickness T-T of less than about 2.5 mm.

While embodiments and applications have been shown and described, it would be apparent to those skilled in the art having the benefit of this disclosure that many more modifications than mentioned above are possible without departing from the inventive concepts disclosed herein. The invention, therefore, is not to be restricted except in the spirit of the appended claims.

What is claimed is:

1. A cochlear fenestration burr, comprising:
    a shaft oriented along a longitudinal axis of rotation of the burr;
    a cylindrical depth stop member oriented along the axis, the depth stop member having a thickness dimension, a diameter dimension and a contact surface;
    an extension member extended outward from the contact surface and coaxial with the axis;
    a cutting member having a cutting surface supported by the extension member;
    a cutting tip at the end of the cutting member in the center of the cutting surface and coaxial with the axis, a maximum diameter of the extension member being less than a maximum diameter of the cutting member;
    a cutting depth defined by a distance along the axis between an end of the cutting tip and the contact surface; and
    a cutting grit disposed on the cutting tip and cutting surface wherein the cutting depth is less than or equal to about 2.5 mm.

2. The device of claim 1, wherein the diameter dimension of the cylindrical depth stop member is less than or equal to about 4.0 mm.

3. The device of claim 2 wherein the cutting grit includes particles of diamond.

4. The device of claim 2, wherein the cutting member comprises titanium.

5. A method for preparing a fenestration in a cochlea of a patient with a fenestration burr, the burr including a shaft disposed along a longitudinal axis of rotation, a depth stop member having a contact surface, height dimension and diameter dimension, and an extension member supporting a cutting member having a cutting surface with a pointed tip, a maximum diameter of the extension member being less than a maximum diameter of the cutting member, the method comprising:
    locating the fenestration burr at a desired location of the fenestration;
    rotating the burr to cut into the cochlea;
    using the tip to lock the burr in position and avoid lateral movement of the burr during the rotating; and
    limiting the depth of the cut made by the burr with the contact surface.

6. The method of claim 5, wherein the cutting surface includes diamond particles.

7. The method of claim 5, wherein the limiting limits the depth to a distance along the axis between an end of the tip and the contact surface.

8. The method of claim 5, further comprising:
    using the diameter of the depth stop member to align the burr during the rotating.

* * * * *